United States Patent
Heifetz

(12) 
(10) Patent No.: US 6,362,398 B1
(45) Date of Patent: Mar. 26, 2002

(54) CLPP PLASTID PROMOTER SEQUENCE

(75) Inventor: Peter Bernard Heifetz, Durham, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/265,919

(22) Filed: Mar. 10, 1999

Related U.S. Application Data

(60) Provisional application No. 60/126,430, filed on Mar. 11, 1998.

(51) Int. Cl.⁷ .................................................. A01H 5/00
(52) U.S. Cl. ..................... 800/298; 435/320.1; 435/419; 536/24.1
(58) Field of Search ....................... 536/24.1; 435/320.1, 435/419, 468; 800/278, 287, 298

(56) References Cited

U.S. PATENT DOCUMENTS

| | | | |
|---|---|---|---|
| 5,451,513 A | 9/1995 | Maliga et al. | 435/172.3 |
| 5,530,191 A | 6/1996 | Maliga et al. | 800/205 |
| 5,545,817 A | 8/1996 | McBride et al. | 800/205 |
| 5,576,198 A | 11/1996 | McBride et al. | 435/91.3 |

FOREIGN PATENT DOCUMENTS

| | | |
|---|---|---|
| WO | WO97/06250 | 2/1997 |
| WO | WO97/32011 | 2/1997 |
| WO | WO97/32977 | 9/1997 |

OTHER PUBLICATIONS

Benfey PN, et al. "The cauliflower mosaic virus 35S promoter: Combinatorial regulation of transcription in plants." Science 250: 959–966, Nov. 1990.*

Kim Y, et al. "A 20 nucleotide upstream element is essential for the nopaline synthase (nos) promoter activity." Plant Mol. Biol. 24: 105–117, 1994.*

Manen et al., The ATPB and RBCL Promoters in Plastid DNAs of a Wide Dicot Range, Journal of Molecular Evolution, 38(6):577–582 Jun. 1994.

Allison et al. "Deletion of rpoB reveals a second distinct transcription system in plastids of higher plants" The EMBO Journal, 15:2802–2809 (1996).

Clarke et al. "Identification and expression of the chloroplast clpP gene in the conifer *Pinus contorta*" Plant Molecular Biology, 26: 851–862 (1994).

Ems et al. "Transcription, splicing and editing of plastid RNAs in the nonphotosynthetic plant *Epifagus virginiana*" Plant Molecular Biology, 29: 721–733 (1995).

Huang et al. "The Chlamydomonas chloroplast clpP gene contains translated large insertion sequences and is essential for cell growth" Mol Gen Genet, 244: 151–159 (1994).

Koop et al. "Integration of foreign sequences into the tobacco plastome via polyethylene glycol–mediated protoplast transformation" Planta, 199: 193–201 (1996).

O'Neill et al. "Chloroplast transformation in plants: polyethylene glycol (PEG) treatment of protoplasts is an alternative to biolistic delivery systems" The Plant Journal, 3(5):729–738 (1993).

Shanklin et al. "The Stroma of Higher Plant Plastids Contain ClpP and ClpC, Functional Homologs of *Eschericha coli* ClpP and ClpA: An Archetypal Two–Component ATP–Dependent Protease" The Plant Cell, 7: 1713–1722 (1995).

Sriraman et al., "The phage–yype PclpP–53 plastid promoter comprises sequences downstream of the transcription initiation site" Nucleic Acids Research 26(21): 4874–4879 (1998).

Sriraman et al., "Transcription from Heterologous rRNA Operon Promoters in Chloroplasts Reveals Requirement for Specific Activating Factors" Plant Physiol. 117:1495–1499 (1998).

Svab et al. "High–frequency plastid transformation in tobacco by selection for a chimeric aadA gene" Proc. Natl. Acad. Sci. USA, 90: 913–917 (1993).

* cited by examiner

Primary Examiner—Amy J. Nelson
(74) Attorney, Agent, or Firm—Marcia R. Morton; J. Timothy Meigs

(57) ABSTRACT

A novel promoter isolated from the 5' flanking region upstream of the coding sequence of the Arabidopsis plastid clpP gene is described. Also described are a novel method for utilizing protein-coding regions of plastid genes to isolate intervening regulatory sequences and a novel method for improving plastid transformation efficiency using exogenous plastid promoters that differ in nucleotide sequence from native plastid promoters.

5 Claims, No Drawings

CLPP PLASTID PROMOTER SEQUENCE

This application claims the benefit of U.S. Provisional Application No. 60/126,430, filed March 11, 1998, incorporated herein by reference.

FIELD OF THE INVENTION

The present invention generally pertains to plant molecular biology and more particularly pertains to a novel plastid promoter isolated from Arabidopsis thaliana and methods of use therefor. The present invention also pertains to a novel method for utilizing protein-coding regions of plastid genes to isolate intervening regulatory sequences. The present invention further pertains to the use of novel plastid promoter sequences to improve plastid transformation efficiency.

BACKGROUND OF THE INVENTION

Plastid transformation, in which genes are inserted by homologous recombination into all of the several thousand copies of the circular plastid genome present in each plant cell, takes advantage of the enormous copy number advantage over nuclear-expressed genes to permit expression levels that may exceed 10% of the total soluble plant protein. In addition, plastid transformation is desirable because plastid-encoded traits are not pollen transmissable; hence, potential risks of inadvertent transgene escape to wild relatives of transgenic plants are obviated. Other advantages of plastid transformation include the feasibility of simultaneous expression of multiple genes as a polycistronic unit and the elimination of positional effects and gene silencing that may result following nuclear transformation. Plastid transformation technology is extensively described in U.S. Pat. Nos. 5,451,513, 5,545,817, 5,545,818, and 5,576,198; in Intl. Application No. WO 95/16783; and in Boynton et al., *Methods in Enzymology* 217: 510–536 (1993), Svab et al., *Proc. Natl. Acad. Sci. USA* 90: 913–917 (1993), and McBride et al., *Proc. Nati. Acad. Sci. USA* 91: 7301–7305 (1994); all of which are incorporated herein by reference.

The basic technique for tobacco plastid transformation involves the particle bombardment of leaf tissue with regions of cloned plastid DNA flanking a selectable marker, such as an antibiotic resistance gene. The 1 to 1.5 kb flanking regions, termed targeting sequences, facilitate homologous recombination with the plastid genome and thus allow the replacement or modification of specific regions of the 156 kb tobacco plastome. Initially, point mutations in the chloroplast 16S rRNA and rpsl 2 genes conferring resistance to spectinomycin and/or streptomycin were utilized as selectable markers for transformation (Svab et al., *Proc. Natl. Acad. Sci. USA* 87: 8526–8530 (1990); Staub, J. M., and Maliga, P., *Plant Cell* 4: 39–45 (1992); both of which are incorporated herein by reference). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P., *EMBO J.* 12: 601–606 (1993), incorporated herein by reference). Substantial increases in transformation frequency were obtained by replacement of the recessive rDNA or r-protein antibiotic resistance genes with a dominant selectable marker, the bacterial aadA gene encoding the spectinomycin-detoxifying enzyme aminoglycoside-3'-adenyltransferase (Svab et al.,1993). Previously, this marker had been used successfully for high-frequency transformation of the plastid genome of the green alga *Chiamydomonas reinhardtii* (Goldschmidt-Clermont, M., *Nucl. Acids Res.* 19: 4083–4089 (1991), incorporated herein by reference). Techniques have also been described for the transfection of plastids in plant protoplasts (O'Neill et al., *Plant Journal* 3(5): 729–738 (1993) and Koop et al., *Planta* 199: 193–201 (1996), both of which are incorporated herein by reference).

An especially preferred plant plastid promoter for use in plastid targeting vectors to express foreign genes in the plant plastid is the clpP gene promoter. The clpP gene encodes the proteolytic subunit of the Clp ATP-dependent protease, which in Arabidopsis is constitutively expressed in the plastids of photosynthetic and nonphotosynthetic plant tissues (Shanklin et al., *The Plant Cell* 7: 1713–1722 (1995)), incorporated herein by reference. clpP is also one of the few plant plastid genes that is retained in the genomes of non-photosynthetic plants (e.g. *Epifagus virginiana*; Morden et al. *EMBO J.* 10: 3281–3288 (1991)) and the clpP message is known to be expressed in the plastids of the barley mutant *albostrians*, which lacks detectable plastid translational activity (Hübschmann and Börner, Plant Mol. Biol. 36: 493–496 (1998)). Hence, the clpP promoter is likely to be active transcriptionally even in non-green plastids. The characterization of the promoter region from the tobacco clpP gene is described in WO 97/06250, incorporated herein by reference. In this reference, the tobacco clpP gene is characterized as having 5' promoter sequences that are recognized by both a nuclear encoded plastid (NEP) RNA polymerase and a plastid encoded plastid (PEP) RNA polymerase. A primary transcript arising from the tobacco clpP promoter sequence mapping to the −53 nucleotide position (upstream from the ATG translation initiation codon) is characterized in WO 97/06250 as being highly expressed in the bleached plastids of tobacco mutants lacking a plastid-encoded RNA polymerase by virtue of deletion of the rpoB gene.

A tobacco clpP promoter sequence has been used to drive expression of a herbicide-resistant form of the Arabidopsis Protoporphyrinogen IX ("PROTOX") gene in the plastids of tobacco (WO 97/32011, incorporated herein by reference). Identical constructs substituting a GUS reporter gene have been introduced into tobacco plastids, demonstrating that clpP-driven expression is not restricted to green plastids but is also found in root plastids (leucoplasts, amyloplasts) and flower plastids (chromoplasts).

Despite the promise shown by plastid transformation, only recently has this technology been applied to plants other than tobacco. International Application No. WO 97/32977, incorporated herein by reference, describes methods and compositions for creating transplastomic plants in the Cruciferae family, such as Brassica and Arabidopsis, using leaf and cotyledon cells. However, what is also needed are novel plastid promoter sequences from plants other than tobacco, particularly Arabidopsis, which can be used to drive the expression of transgenes in green and non-green plastids of Arabidopsis and any other plant species.

SUMMARY OF THE INVENTION

In view of the above, one object of the invention is to provide a novel plastid promoter from *Arabidopsis thaliana* that is functional in all plastid types. Another object of the invention is to provide a method for utilizing protein-coding regions of plastid genes to isolate novel intervening regulatory sequences, such as novel promoter sequences or untranslated 3' or 5' RNA sequences. Still another object of the invention is to use novel plastid promoter sequences to improve plastid transformation efficiency by reducing undesired homologous recombination between native DNA sequences in the plastid genome and exogenous DNA sequences contained in chimeric DNA fragments incorporated into plastid transformation vectors.

In furtherance of these and other objects, the present invention provides a nucleic acid promoter isolated from the 5' flanking region upstream of the coding sequence of the Arabidopsis plastid clpP gene. In a preferred embodiment, the nucleic acid promoter of the invention is substantially similar to a promoter sequence downstream of nucleotide number 263 of SEQ ID NO:1. In a more preferred embodiment, the nucleic acid promoter of the invention has sequence identity with a promoter sequence downstream of nucleotide number 263 of SEQ ID NO:1. In still another embodiment, the nucleic acid promoter of the invention is substantially similar to SEQ ID NO:1. In yet another embodiment, the nucleic acid promoter of the invention is comprised within SEQ ID NO:1. In still another embodiment, the nucleic acid promoter of the invention comprises a 20 base pair nucleotide portion identical in sequence to a consecutive 20 base pair nucleotide portion of SEQ ID NO:1. The present invention also encompasses a chimeric gene comprising the nucleic acid promoter of the invention operatively linked to the coding sequence of a gene of interest; a plant transformation vector comprising such a chimeric gene; and a transgenic plant, plant cell, plant seed, plant tissue, or plant plastid, each comprising such a chimeric gene.

In another aspect, the present invention provides a novel method for isolating intervening regulatory DNA sequences from between the protein-coding regions of two plastid genes, comprising the steps of:

(a) determining the relative orientation and either a degenerate or a specific nucleotide sequence of protein-coding regions of two plastid genes;

(b) designing a first degenerate or specific PCR primer based on the determined sequence of the protein-coding region of one of the two plastid genes;

(c) designing a second degenerate or specific PCR primer based on the determined sequence of the protein-coding region of the other of the two plastid genes;

(d) amplifying a DNA fragment using the primers of steps (b) and (c), whereby the amplified DNA fragment comprises an intervening regulatory DNA sequence from between the protein-coding regions of the two plastid genes.

In a preferred embodiment of this method, the two plastid genes are a clpP gene and a psbB gene. According to this embodiment, the intervening regulatory DNA sequence comprises a clpP promoter. In another preferred embodiment of this method, the two plastid genes are a 16S rRNA gene and a valine tRNA gene. According to this embodiment, the intervening regulatory DNA sequence comprises a 16S rRNA promoter.

In yet another aspect, the present invention provides an improved plastid transformation method, comprising transforming a plastid of a host plant species with a chimeric gene comprising a plastid-active regulatory sequence operatively linked to a coding sequence of interest, wherein the regulatory sequence has a nucleotide sequence that is less than approximately 90% identical to a corresponding native regulatory sequence in the host plant plastid, whereby undesired somatic recombination between the regulatory sequence in the chimeric gene and the corresponding native regulatory sequence in the host plant plastid is reduced. In a preferred embodiment of this method, the chimeric gene is isolated from the plastid genome of the host plant species and at least approximately 10% of the nucleotides of the regulatory sequence have been mutated. In another preferred embodiment of this method, the regulatory sequence in the chimeric gene is isolated from the plastid genome of a different plant species than the host plant species. For example, the regulatory sequence in the chimeric gene may be isolated from the plastid genome of Arabidopsis. In one especially preferred embodiment, the regulatory sequence in the chimeric gene is a nucleic acid promoter isolated from the 5' flanking region upstream of the coding sequence of the Arabidopsis clpP gene. In another especially preferred embodiment, the regulatory sequence in the chimeric gene is a nudeic acid promoter isolated from the 5' flanking region upstream of the coding sequence of the Arabidopsis 16S rRNA gene.

Other objects and advantages of the invention will become apparent to those skilled in 4t the art from a study of the following description of the invention and non-limiting examples.

DESCRIPTION OF THE SEQUENCES IN THE SEQUENCE LISTING

SEQ ID NO: 1 is the nucleotide sequence of the Arabidopsis clpP gene promoter region.

SEQ ID NO:2 is primer A_clpP used in Example 1.

SEQ ID NO:3 is primer A_psbB used in Example 1.

SEQ ID NO:4 is primer Aclp_P1a used in Example 2.

SEQ ID NO:5 is primer Acip_P2b used in Example 2.

SEQ ID NO:6 is primer rps16P_1a used in Example 2.

SEQ ID NO:7 is primer rps16P_1b used in Example 2.

SEQ ID NO:8 is the top-strand primer used in Example 3.

SEQ ID NO:9 is a bottom-strand primer used in Example 3.

SEQ ID NO:10 is the nucleotide sequence of the Arabidopsis 16S rRNA gene promoter region.

SEQ ID NO:11 is a top-strand primer used in Example 4.

SEQ ID NO:12 is a bottom-strand primer used in Example 4.

DEFINITIONS

For clarity, certain terms used in the specification are defined and presented as follows:

Associated With/Operatively Linked: refers to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

Chimeric Gene/Fusion Sequence: a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid sequence of the chimeric gene is not normally operatively linked to the associated nucleic acid sequence as found in nature.

Coding Sequence: nucleic acid sequence that is transcribed into RNA such as mRNA, rRNA, tRNA, snRNA, sense RNA or antisense RNA. Preferably the RNA is then translated in an organism to produce a protein.

Gene: a defined region that is located within a genome and that, besides the aforementioned coding sequence, comprises other, primarily regulatory, sequences responsible for the control of the expression, that is to say the transcription and translation, of the coding portion. A gene may also comprise other 5' and 3' untranslated sequences and termination sequences. Further elements that may be present are, for example, introns.

Gene of Interest: any gene that, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

Heterologous Nucleic Acid Sequence: a nucleic acid sequence not naturally associated with the host genome into which it is introduced, including non-naturally occurring multiple copies of a naturally occurring nucleic acid sequence.

Homologous Nucleic Acid Sequence: a nucleic acid sequence naturally associated with a host genome into which it is introduced.

Homologous Recombination: the reciprocal exchange of nucleic acid fragments between homologous nucleic acid molecules.

Isolated: in the context of the present invention, an isolated nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a transgenic host cell.

Minimal Promoter: promoter elements that are inactive or that have greatly reduced promoter activity in the absence of upstream activation. In the presence of a suitable transcription factor, the minimal promoter functions to permit transcription.

Nucleic Acid Molecule I Nucleic Acid Sequence: a linear segment of single- or double-stranded DNA or RNA that can be isolated from any source. In the context of the present invention, the nucleic acid molecule is preferably a segment of DNA.

Plant: any plant at any stage of development, particularly a seed plant.

Plant Cell: a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

Plant Cell Culture: cultures of plant units such as, for example, protoplasts, cell culture cells, cells in plant tissues, pollen, pollen tubes, ovules, embryo sacs, zygotes and embryos at various stages of development.

Plant material: leaves, stems, roots, flowers or flower parts, fruits, pollen, egg cells, zygotes, seeds, cuttings, cell or tissue cultures, or any other part or product of a plant.

Plant Organ: a distinct and visibly structured and differentiated part of a plant such as a root, stem, leaf, flower bud, or embryo.

Plant tissue: as used herein means a group of plant cells organized into a structural and functional unit. Any tissue of a plant in *planta* or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

Promoter: an untranslated DNA sequence upstream of the coding region that contains the binding site for RNA polymerase 11 and initiates transcription of the DNA. The promoter region may also include other elements that act as regulators of gene expression.

Protoplast: an isolated plant cell without a cell wall or with only parts of the cell wall.

Regulatory Sequence: an untranslated nucleic acid sequence that assists in, enhances, or otherwise affects the transcription, translation or expression of an associated structural nucleic acid sequence that codes for a protein or other gene product. Regulatory sequences include promoters. A promoter sequence is usually located at the 5' end of a translated sequence, typically between 20 and 100 nucleotides from the 5' end of the translation start site. Regulatory sequences may also include transcribed but untranslated nucleic acid sequences located 5' and 3' to coding sequences. These untranslated RNA's are typically involved in post-transcriptional regulation of gene expression.

Substantially Similar: with respect to nucleic acids, a nucleic acid molecule that has at least 60 percent sequence identity with a reference nucleic acid molecule. In a preferred embodiment, a substantially similar DNA sequence is at least 80% identical to a reference DNA sequence; in a more preferred embodiment, a substantially similar DNA sequence is at least 90% identical to a reference DNA sequence; and in a most preferred embodiment, a substantially similar DNA sequence is at least 95% identical to a reference DNA sequence. A substantially similar nucleotide sequence typically hybridizes to a reference nucleic acid molecule, or fragments thereof, under the following conditions: hybridization at 7% sodium dodecyl sulfate (SDS), 0.5 M $NaPO_4$ pH 7.0, 1 mM EDTA at 50° C.; wash with 2×SSC, 1% SDS, at 50° C. With respect to proteins or peptides, a substantially similar amino acid sequence is an amino acid sequence that is at least 90% identical to the amino acid sequence of a reference protein or peptide and has substantially the same activity as the reference protein or peptide.

Tolerance: the ability to continue normal growth or function when exposed to an inhibitor or herbicide.

Transformation: a process for introducing heterologous DNA into a cell, tissue, or plant, including a plant plastid. Transformed cells, tissues, or plants are understood to encompass not only the end product of a transformation process, but also transgenic progeny thereof.

Transformed/Transgenic/Recombinant: refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (lle; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Furthermore, (Xaa; X) represents any amino acid.

DETAILED DESCRIPTION OF THE INVENTION

The present invention provides the promoter region for the clpP gene from the *Arabidopsis thaliana* plastid genome that encodes a plant homologue of the Clp ATP-dependent protease. The disclosed promoter can be used to drive expression of coding sequences for selectable marker genes or any other genes of interest in the plastids of transgenic plants. The promoter of the present invention is useful for constitutive expression of transgenes in both green and non-green plastids and is therefore particularly useful for plastid transformation in plants such as maize, in which selection of regenerable transformants requires selection in non-green tissues.

The Arabidopsis clpP promoter of the present invention can be incorporated into plastid transformation vectors and transformed into plastids according to methods known in the art, particularly those described in the following: U.S. Pat. Nos. 5,451,513, 5,545,817, 5,545,818, and 5,576,198; Intl. Application Nos. WO 95/16783, WO 97/32011, and WO 97/32977; and Svab et al. (1993) and McBride et al. (1994).

The present invention also provides a novel method for utilizing protein-coding regions of plastid genes to isolate novel intervening regulatory sequences, such as novel promoters or 3' or 5' UTR's. Such a method is exemplified by Applicant's technique for isolating the Arabidopsis plastid clpP promoter region and the Arabidopsis plastid 16S rRNA promoter region, as set forth in detail in the Examples below. Briefly, isolation of these promoter regions is facilitated by the chance that gene order in the Arabidopsis plastid genome is conserved relative to that of *Nicotiana tabacum*, for which the entire plastid genome sequence is known. In tobacco, clpP is present in divergent orientation from the psbB gene, the coding sequence of which is conserved among a number of plant species. Because only 445 base pairs separate the psbB start codon from the divergently oriented start codon of clpP in tobacco, the sequences of the protein coding regions of the divergent clpP and psbB genes are used to design primers for PCR that amplify the noncoding intergenic region between these genes. This region includes the promoters for psbB in one orientation and clpP in the other. An expressed sequence tag (EST) sequence from Arabidopsis is found in an EST database that appears to include a portion of the clpP coding sequence and 5' untranslated RNA (5'UTR). The sequence of this EST is used to design primers for PCR amplification of the clpP promoter based on the Arabidopsis DNA sequence encoding the putative start of the clpP protein. These primers were paired with ones designed to match the highly conserved DNA sequences around the psbB start codon. Using these primers, a DNA fragment of approximately 500 nucleotides, which includes the Arabidopsis plastid clpP promoter region, is amplified from total DNA of Arabidopsis. A DNA fragment that includes the Arabidopsis plastid 16S rRNA promoter region is amplified in a like manner.

Using the above method, one of ordinary skill in the art can use the protein-coding regions of two nearby plastid genes to isolate intervening untranslated sequences such as promoters and other regulatory sequences from the plastid genome of any plant. Preferably the two plastid genes are adjacent, in that there are no other transcribed sequences between the two nearby plastid genes; however, it is foreseeable that this method will work even if there is a small gene, such as a gene encoding a tRNA, in the amplified region between the two nearby plastid genes. In a preferred embodiment, one of ordinary skill in the art can use the above method to isolate a plastid clpP promoter from the plastid genome of any plant. In another preferred embodiment, one of ordinary skill in the art can use the above method to isolate a plastid 16S rRNA promoter from the plastid genome of any plant.

The present invention further provides a method of using novel plastid promoters, such as the Arabidopsis plastid clpP or 16S rRNA promoters, to improve plastid transformation efficiency by reducing undesired recombination between native DNA sequences in the plastid genome and exogenous DNA sequences contained in chimeric DNA fragments that are incorporated into plastid transformation vectors. It is known that even relatively short regions of homology between native DNA sequences in the plastid genome and exogenous DNA sequences will ultimately cause somatic recombination in plastid transformants. This biological property has even been used as a means for eliminating selectable markers from plastid transformants in chloroplasts of the green alga Chlamydomonas by flanking the selectable marker with identical repeated heterologous DNA sequences. Although neither the minimum size tract of homology required nor the precise degree of sequence identity within a particular homology tract sufficient for recombination has been identified, as little as 50-bp of homology to the plastid genome may be enough to induce recombination. These recombination events are visible in transgenic plants as pale sectors in leaves resulting from division of cells in which plastid genome rearrangements have occurred. In extreme cases the result is nearly white leaves with small patches of green indicating recombination occurring in the majority of somatic cells and their lineage.

The essential features of non-recombinogenic regulatory sequences (such as promoters and 5' and 3' UTR's) include both the ability to function correctly to control heterologous gene expression in the plastids of a plant species of interest, as well as the lack of sufficient sequence identity to promote homologous plastid recombination. The latter property may be achieved either by using a heterologous regulatory sequence derived from the plastid genome of a different plant species, which has diverged in sequence to less than 85–90% identity, or by sufficiently mutating a native regulatory sequence derived from the plastid genome of the same plant species. In one embodiment this method involves using the Arabidopsis clpP promoter of the present invention to direct transcription of genes of interest in the plastids of heterologous plant species such as tobacco, maize, rice, soybean, tomato, potato, or others. In another embodiment this method involves using the Arabidopsis 16S rRNA promoter described in the Examples to direct transcription of genes of interest in the plastids of heterologous plant species such as tobacco, maize, rice, soybean, tomato, potato, or others. In addition to higher plant plastid genes, useful heterologous promoters or 5' and 3' UTR's for non-recombinogenic regulation of plastid transgenes may also be derived from plastid genes of lower plants or algae, chromosomal genes of cyanobacteria, or genomes of viruses that infect plant or algal chloroplasts or cyanobacterial cells.

Selection of mutated native genes from the same plant, which are incapable of undesired recombination, is facilitated by random mutagenesis of regulatory sequences such that the sequence identity is reduced to at most 90% relative to the starting sequence. The pool of randomly mutated regulatory sequences is then selected for the subset that still is plastid-active (capable of normal functioning in plant plastids) by cloning each mutant upstream of a selectable marker gene that operates in the plastid then transforming the entire pool of chimeric DNA's into the plastids of wildtype plants. Only those mutated sequences still capable of functioning in plastids will result in expression of the selectable marker in the transgenic plants. Transgenic plants expressing the selectable marker are also assessed for somatic recombination by observing the frequency of leaf sectoring. The targeted region of the plastid genome of a transformed plant expressing the selectable marker and having a desirable frequency of leaf sectoring is then sequenced to determine which mutated regulatory sequence is present. This mutated sequence thus meets the criteria of controlling expression in a plastid of a gene of interest and having sufficient sequence divergence relative to native plastid DNA sequences to reduce the frequency of undesired recombination.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), *Current Protocols in Molecular Biology*, John Wiley and Sons, Inc. (1994); T. Maniatis, E. F. Fritsch and J. Sambrook, *Molecular Cloning: A Laboratory Manual*, Cold Spring Harbor laboratory, Cold Spring Harbor, N.Y. (1989); and by T. J. Silhavy, M. L. Berman, and L. W. Enquist, *Experiments with Gene Fusions*, Cold Spring Harbor Laboratory, Cold Spring Harbor, N.Y. (1984).

Example 1

Isolation of the Arabidopsis clpP Promoter Region

Isolation of the Arabidopsis clpP promoter region is facilitated by the chance that gene order in the Arabidopsis plastid genome is conserved relative to that of *Nicotiana tabacum*, a plant for which the entire plastid genome sequence is known. In tobacco, clpP is present in divergent orientation from the psbB gene, which has been sequenced from a number of plant species and shown to be conserved in sequence. An alignment of the psbB sequences of tobacco, maize, wheat, and *Nicotiana acumina* indicates that the first eight amino acids are identically conserved, as are their DNA coding sequences. In tobacco only 445 base pairs separate the psbB start codon from the divergently oriented start codon of clpP.

In view of the above, the Applicant postulates that the sequences of the protein-coding regions of the divergent clpP and psbB genes can be used to design primers for PCR that could amplify the noncoding intergenic region between these genes. This region will, in theory, include the promoters for psbB in one orientation and clpP in the other. An expressed sequence tag (EST) sequence from Arabidopsis is found in the TIGR NHC AtEST database (http://www.tigr.org) that appears to include a portion of the clpP coding sequence and 5' untranslated RNA (5'UTR). Because the putative translation of this sequence is similar to the mature clpP of *E. coli*, and hence does not appear to include a plastid transit peptide, it is postulated that this EST (Seq ID#P_3982 from the TIGR NHC AtEST database) represents a portion of the plastid clpP message. However, because Shanklin et al. (1995) have suggested that nuclear-encoded clpP homologs might exist in Arabidopsis, the Applicant is wary of finding these instead of the genuine plastid-encoded gene. Because EST's by definition come from expressed messages, ESTP_3982 is not expected to include any of the untranscribed clpP promoter region.

The nucleotide sequence of ESTP_3982 is used to design primers for PCR amplification of the clpP promoter based on the Arabidopsis DNA sequence encoding the start of the clpP protein in this plant. These primers are paired with ones designed to match the highly conserved DNA sequences around the psbB start codon, which Applicant postulates are similarly conserved in Arabidopsis. The primers used are:

A_clpP:
   5'-AAGGGACTTTTGGAACGCCAATAGGCAT-3'
   (SEQ ID NO:2) and

A_psbB: 5'-CACGATACCAAGGCAAACCCATGGA-3' (SEQ ID NO:3).

These successfully amplify a DNA fragment of approximately 500 nucleotides from total DNA of *A. thaliana* (cv "Landsburg erecta") using Pfu thermostable DNA polymerase. The blunt-ended DNA fragment is sequenced both directly (using the cloning primers) and subsequent to cloning into the EcoRV site of vector pGEM5Zf(–) to construct plasmid pPH146b. The nucleotide sequence of this approximately 500-bp PCR fragment is given in SEQ ID NO: 1. Sequence analysis reveals 86% sequence identity to the tobacco clpP promoter region over a 200-bp region extending upstream of the clpP start codon. Thus, SEQ ID NO:1 includes the Arabidopsis clpP promoter region.

Example 2

Preparation of a Chimeric Gene Containing the Arabidopsis clpP Promoter and Native clpP 5' Untranslated Sequence Fused to a GUS Reporter Gene and Tobacco Plastid rps16 Gene 3' Untranslated Sequence in a Plastid Transformation Vector I. Amplification of the Arabidopsis Plastid clpP Gene Promoter and Complete 5' Untranslated RNA (5' UTR).

DNA from plasmid pPH146b is used as the template for PCR with a left-to-right "top strand" primer comprising an introduced EcoRI restriction site at position –234 relative to the ATG start codon of the Arabidopsis plastid clpP gene (nucleotide no. 263 of SEQ ID NO: 1) (primer Aclp_P_1a: 5'-GCGGAATTCATCATTCAGAAGCCCGTTCGT-3' (SEQ ID NO:4; EcoRI restriction site underlined)) and a right-to-left "bottom strand" primer homologous to the region from –21 to –1 relative to the ATG start codon of the clpP promoter that incorporates an introduced BspHI restriction site at the start of translation (primer AclpP_2b: 5'-GCGTCATGAAATGAAAGAAAAAGAGAAT-3' (SEQ ID NO:5; BspHI restriction site underlined)). This PCR reaction is undertaken with Pfu thermostable DNA polymerase (Stratagene, La Jolla Calfi.) in a Perkin Elmer Thermal Cycler 480 according to the manufacturer's recommendations (Perkin Elmer/Roche, Branchburg, N.J.) as follows: 7 min 95° C., followed by 4 cycles of 1 min 95° C./2 min 43° C./1 min 72° C., then 95° C./2 min 55° C./1 min 72° C. A 250 bp amplification product comprising the promoter and 5' untranslated region of the Arabidopsis clpP gene containing an EcoRI site at its left end and an BspHI site at its right end with two modifications near the ATG to correspond with the tobacco clpP sequence 5' UTR is gel purified using standard procedures and digested with EcoRI and BspHI (all restriction enzymes may be purchased from New England Biolabs, Beverly, Mass.).

II. Amplification of the Tobacco Plastid rps16 Gene 3' Untranslated RNA Sequence (3'UTR).

Total DNA from *N. tabacum* c.v. "Xanthi NC" is used as the template for PCR as described above with a left-to-right "op strand" primer comprising an introduced XbaI restriction site immediately following the TAA stop codon of the plastid rps16 gene encoding ribosomal protein S16 (primer rps16P_1a: 5'-GCG TCTAGATCAACCGAAATTCAATTAAGG-3' (SEQ ID NO:6; XbaI restriction site underlined)) and a right-to-left "bottom strand" (primer homologous to the region from +134 to +151 relative to the TAA stop codon of rps16 that incorporates an introduced HindIII restriction site at the 3' end of the rps16 3' UTR (primer rps16P_1b: 5'-CGCGCTTCAATGGAAGCAATGATAA-3' (SEQ ID NO:7; HindIII restriction site underlined)). The amplification product comprising the 3' untranslated region of the rps16 gene containing an XbaI site at its left end and a HindIII site at its right end and containing the region corresponding to nucleotides 4943 to 5093 of the *N. tabacum* plastid DNA sequence (Shinozaki et al., 1986) is gel purified and digested with XbaI and HindIII.

III. Ligation of a GUS Reporter Gene Fragment to the clpP Gene Promoter and 5' and 3'UTR's.

An 1864 bp βglucuronidase (GUS) reporter gene fragment derived from plasmid pRAJ275 (Clontech) containing an NcoI restriction site at the ATG start codon and an XbaI site following the native 3' UTR is produced by digestion with NcoI and XbaI. This fragment is ligated in a four-way reaction to the 250 bp EcoRI/BspHI Arabidopsis clpP promoter fragment, the 157 bp XbaI/HindIII tobacco ips16 3'UTR fragment, and a 3148 bp EcoRI/HindIII fragment from cloning vector pGEM3Zf(-) (Promega, Madison Wis.) to construct plasmid pPH165. Plastid transformation vector pPH166 is constructed by digesting plasmid pPRV111a (Zoubenko et al. 1994) with EcoRI and HindIII and ligating the resulting 7287 bp fragment to a 2222 bp EcoRI/HindIII fragment of pPH165.

Example 3

Isolation of the Arabidopsis 16S rRNA Gene Promoter Region

Isolation of the Arabidopsis 16S rRNA gene promoter region is facilitated by the chance that gene order in the Arabidopsis plastid genome is conserved relative to that of *Nicotiana tabacum*, a plant for which the entire plastid genome is known. In *Sinapis alba*, a closely related species to Arabidopsis, the 16S rRNA gene and valine tRNA are oriented as in tobacco (GenBank assession number CHSARRN1). The Arabidopsis 16S rRNA gene promoter region is isolated by PCR amplification (PfuTurbo DNA Polymerase, Stratagene, La Jolla, Calfi.) using total *A. thaliana* (cv "Landsburg erecta") as template and the following primers that are conserved in both Nicotiana and *Sinapis alba*: "top strand" primer (5'-CAGTTCGAGCCTGATTATCC-3' (SEQ ID NO:8) and the "bottom strand" primer (5'-GTTCTTACGCGTTACTCACC-3' (SEQ ID NO:9). The predicted 379 bp (based on *Sinapis alba* sequence) amplification product comprising the Arabidopsis 16S rRNA gene promoter region corresponding to nucleotides 102508 to 102872 of the tobacco plastid genome (Shinozaki et al., 1986) is blunt end ligated into the EcoRV site of pGEM5Zf (-) (Promega) to construct pArab16S and sequence analysis and comparisons to the tobacco 16S rRNA promoter is performed. The Arabidopsis 16S rRNA gene promoter region product is 369 bp and is set forth as SEQ ID NO:10.

Example 4

Preparation of a Chimeric Gene Containing the Arabidopsis 16S rRNA Gene Promoter and Native 5' Untranslated Sequence Fused to the Ribosome Binding Site of the Tobacco rbcL gene, a GUS Reporter Gene and the Tobacco Plastid rps16 Gene 3' Untranslated Sequence in a Plastid Transformation Vector I. Amplification of the Arabidopsis Plastid 16S rRNA Gene Promoter and Native 5' Untranslated Sequence (5' UTR) and Fusion to the Ribosome Binding Site of the Tobacco rbcL gene.

DNA from plasmid pArabl 6S is used as the template for PCR with a "top strand" primer comprising an introduced EcoRI restriction site at the 5' end of the 16S rRNA gene promoter region (position 63 of SEQ ID NO:10) (5'-GCCG GAATTCTCGCTGTGATCGAATAAGAATG-3' (SEQ ID NO:11; EcoRI restriction site underlined)). The "bottom strand" primer extends to position 172 (SEQ ID NO:10) of the 16S rRNA gene promoter 5' untranslated region, mutates three ATG's downstream of the transcription start site by changing position 151 (T to G) (SEQ ID NO: 10), position 158 (A to C) (SEQ ID NO:10 and position 167 (A to C) (SEQ ID NO:10), fuses the ribosome binding site of the tobacco rbcL gene (positions 57569 to 57585) (Shinozaki et al., 1986) as a 5' extension to the 3' end of the 16S rRNA gene 5' UTR and introduces a BspHI site at the 3' end of the ribosome binding site (5'-GCCT TCATGAATCCCTCCCTACAACTATCCAGGCGCTTCAGATTCGCCT (SEQ ID NO:12; BspHI restriction site underlined)). PCR amplification is performed with the Pfu Turbo DNA Polymerase kit (Stratagene). The 145 bp amplification product comprising the Arabidopsis 16S rRNA gene promoter and 5' untranslated region with three ATG's mutated and the ribosome binding site of the tobacco rbcL gene is gel purified and digested with EcoRI and BspHI, yielding a 131 bp product.

II. Ligation of the Arabidopsis 16S rRNA Gene Promoter, 5' UTR and Ribosome Binding Site of the Tobacco rbcL gene to the GUS Reporter Gene and Tobacco Plastid rps16 Gene 3' Untranslated Region (3' UTR) in a Plastid Transformation Vector.

An 1864 bp b-glucuronidase (GUS) reporter gene fragment derived from plasmid pRAJ275 (Clontech) containing an NcoI restriction site at the ATG start codon and an XbaI site following the stop codon is produced by digestion with NcoI and XbaI. This fragment is ligated in a four-way reaction to the 131 bp EcoRI/BspHI Arabidopsis 16S rRNA gene promoter, 5' UTR and tobacco rbcL ribosome binding site fragment, the XbaI/HindIII tobacco rps16 3' UTR fragment described in Example 2, and a 3148 bp EcoRI/HindIII fragment from cloning vector pGEM3Zf(-) (Promega, Madison, Wis.). A plastid transformation vector is constructed by digesting the previous construct with EcoRI and HindIII and ligating the resulting 2.1 kb fragment to a 7.3 kb EcoRI/HindIII fragment from plasmid pPRV111a (Zoubenko et al. 1994).

Example 5

Biolistic Transformation of the Tobacco Plastid Genome

Seeds of *Nicotiana tabacum* c.v. 'Xanthi nc' are germinated seven per plate in a 1" circular array on T agar medium and bombarded 12–14 days after sowing with 1 µm tungsten particles (M10, Biorad, Hercules, Calfi.) coated with DNA from the plasmids described above in Example 2 and Example 4essentially as described in Svab, Z. and Maliga, P. ((1993) *PNAS* 90, 913–917). Bombarded seedlings are incubated on T medium for two days after which leaves are excised and placed abaxial side up in bright light (350–500 µmol photons/m$^2$/s) on plates of RMOP medium (Svab, Z., Hajdukiewicz, P. and Maliga, P. (1990) PNAS 87, 8526–8530) containing 500 µg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots are isolated and subcloned. Complete segregation of transformed plastid genome copies (homoplasmicity) in independent subclones is assessed by standard techniques of Southern blotting (Sambrook et al., (1989) *Molecular Cloning: A Laboratory Manual*, Cold Spring Harbor Laboratory, Cold Spring Harbor). BamHI/EcoRI-digested total cellular DNA (Mettler, I. J. (1987) *Plant Mol Biol Reporter* 5, 346–349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) PNAS 91, 7301–7305) and transferred to the greenhouse.

Various modifications of the invention described herein will become apparent to those skilled in the art. Such modifications are intended to fall within the scope of the appended claims.

What is claimed is:

1. An isolated nucleic acid molecule comprising a nucleic acid promoter comprising nucleotides 6 to 499 of SEQ ID NO: 1.

2. An isolated nucleic acid promoter comprising nucleotides 6 to 499 of SEQ ID NO: 1.

3. A chimeric gene comprising the nucleic acid molecule of claim 1 operatively linked to the coding sequence of a gene of interest.

4. A plant transformation vector comprising the chimeric gene of claim 3.

5. A transgenic plant, plant cell, plant seed, plant tissue, or plant plastid, comprising the chimeric gene of claim 3.

* * * * *

SEQUENCE LISTING

```
<160> NUMBER OF SEQ ID NOS: 12

<210> SEQ ID NO 1
<211> LENGTH: 499
<212> TYPE: DNA
<213> ORGANISM: Arabidopsis thaliana
<220> FEATURE:
<221> NAME/KEY: misc_feature
<222> LOCATION: (497)..(499)
<223> OTHER INFORMATION: clpP ATG start codon
<220> FEATURE:
<221> NAME/KEY: misc_feature
<222> LOCATION: Complement((6)..(8))
<223> OTHER INFORMATION: psbB ATG start codon

<400> SEQUENCE: 1
aaacccatgg aaatacccct ttatcaacga aaaatagaca ctatgtaact ttattgcatt        60
ggaaaaaact atgctacgta cccccccttt ttaggtaatt atttcggaga aaggattaat      120
atttgttcta ttctgttagt aataatggaa caattcaatt catagaaaaa aagggaagcg      180
gatctattct atatccgata agtaccaata tgcaatgggg gttaatccta ttttctatga      240
accaagatag ctattgttgt tgatcattca gaagcccgtt cgtaaaaaat ttcctttagt      300
tttattcatt ctctcttact ttacttttat tttatatttt atttttagctt attcaactta      360 tgtattaaat atcattaatt taaatatgat taataaagta ggaaaaaagg ataatagtat      420
taaaaaacga aaccccaatt ttacgtttcc acatcaaagt gaaatagaga acttcattct      480
cttttttttt catttcatg                                                   499

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: A_clpP PCR
      primer derived from ESTP_3982

<400> SEQUENCE: 2
aagggacttt tggaacgcca ataggcat                                          28
```

```
<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: A_psbB PCR
      primer derived from conserved DNA sequences around
      the psbB start codon

<400> SEQUENCE: 3
cacgatacca aggcaaaccc atgga                                          25

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer
      Aclp_p1a

<400> SEQUENCE: 4
gcggaattca tcattcagaa gcccgttcgt                                     30

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Primer
      Aclp_P2b

<400> SEQUENCE: 5
gcgtcatgaa atgaaagaaa aagagaat                                       28

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer
      rps16P_1a

<400> SEQUENCE: 6
gcgtctagat caaccgaaat tcaattaagg                                     30

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Primer
      rps16_1b

<400> SEQUENCE: 7
cgcaagcttc aatggaagca atgataa                                        27

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: top strand
      primer

<400> SEQUENCE: 8
cagttcgagc ctgattatcc                                                20
```

```
<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: bottom
      strand primer

<400> SEQUENCE: 9
gttcttacgc gttactcacc                                              20

<210> SEQ ID NO 10
<211> LENGTH: 369
<212> TYPE: DNA
<213> ORGANISM: Arabidopsis thaliana

<400> SEQUENCE: 10
cagttcgagc ctgattatcc ctaaacccaa tgaatgtgag tttttctatt ttgacttgct   60
ccctcgctgt gatcgaataa gaatggataa gaggctcgtg ggattgacgt gaggggtag    120 gggtagctat atttctggga gcgaactcca tgcgaatatg aagcgcatgg atacaagtta   180
tgacttggaa tgaaagacaa ttccgaatca gctttgtcta cgaagaagga agctataagt   240
aatgcaacta tgaatctcat ggagagttcg atcctggctc aggatgaacg ctggcggcat   300
gcttaacaca tgcaagtcgg acgggaagtg gtgtttccag tggcggacgg gtgagtaacg   360
cgtaagaac                                                          369

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: top strand
      primer

<400> SEQUENCE: 11
gccggaattc tcgctgtgat cgaataagaa tg                                32

<210> SEQ ID NO 12
<211> LENGTH: 55
<212> TYPE: DNA
<213> ORGANISM: Artificial Sequence
<220> FEATURE:
<223> OTHER INFORMATION: Description of Artificial Sequence: bottom
      strand primer

<400> SEQUENCE: 12
gccttcatga atccctccct acaactatcc aggcgcttca gattcgcctg gagtt        55
```